United States Patent [19]

Swim et al.

[11] Plant 4,670

[45] Mar. 17, 1981

[54] ROSE PLANT

[75] Inventors: Herbert C. Swim; Jack E. Christensen, both of Ontario, Calif.

[73] Assignee: Armstrong Nurseries, Inc., Ontario, Calif.

[21] Appl. No.: 106,723

[22] Filed: Dec. 26, 1979

[51] Int. Cl.[3] ..... A01H 5/00

[52] U.S. Cl. ..... Plt./14

[58] Field of Search ..... Plt./14, 23

*Primary Examiner*—Robert E. Bagwill

*Attorney, Agent, or Firm*—William H. Elliott, Jr.; Andrew R. Klein

[57] ABSTRACT

A new hardy variety of hybrid grandiflora rose plant, of the outdoor, bush type, having a strong citrus fragrance and blooming abundantly almost throughout the growing season. Blooms are borne sometimes singly but usually three to five on a stem, and display color effects predominantly of off-white, suffusing to yellow-green. Flowers range from 3 to 3½ inches across, with from 25 to 30 petals, plus 0 to 5 petaloids.

1 Drawing Figure

This invention relates to a new variety of hybrid grandiflora rose. The plant is a half hardy bush outdoor seedling grown mainly for garden decoration. It was asexually reproduced by Herbert C. Swim and Jack E. Christensen in Ontario, Calif., having as its seed parent "Angel Face" (U.S. Plant Pat. No. 2,792) and for its pollen parent "Misty" (U.S. Plant Pat. No. 3,983). The new variety holds its distinguishing characteristics through succeeding propagations by budding.

The plant bears its flowers sometimes singly, sometimes three to five or more to a stem in irregular flat clusters on normal, short to medium stems. It blooms abundantly outdoors, and nearly continuously during the growing season. The blooms have a strong citrus fragrance.

Among the ways in which this new cultivar may be most readily distinguished from its seed parent, Angel Face, are the following.

Whereas Angel Face bears buds and blooms of a deep lavender coloration, the new cultivar bears buds and blooms of a white coloration, essentially as described below and illustrated herein.

Angel Face bears significantly larger open flowers (4 inches in diameter) than does the new cultivar, whose open flowers are from 3 to 3½ inches in diameter.

Whereas Angel Face is classified as a hybrid floribunda, the new rose is in the hybrid grandiflora class.

This new cultivar may most readily be distinguished from its pollen parent, Misty, by the following characteristics:

Whereas Misty bears flowers of from 35 to 45 petals, the new rose bears blooms of significantly fewer petals, from 25 to 30.

Misty is classified as a hybrid tea, whereas the new cultivar falls into the hybrid grandiflora classification.

Whereas the new cultivar produces flowers of a very strong fragrance, Misty bears flowers of only slight fragrance.

The accompanying drawing illustrates the plant in color and shows the flowering thereof from bud to full bloom.

Throughout this specification color names beginning with a small letter signify that the name of that color, as used in common speech, is aptly descriptive. Color names beginning with a capital letter designate values based upon the Nickerson Color Fan, put out by Munsell Color Co.

BUD

The peduncle is of average length, average caliper, erect and stiff. It is almost smooth, with some stipitate glands. The color is between Moderate Yellow Green, 5GY5/6, and moderate Olive Green, 7.5GY4/4.

Before the calyx breaks, the bud is medium in size, medium-length, pointed, ovoid, and with a few stipitate glands on the surface of the bud. There are usually slender foliaceous parts extending beyond the tip of the bud equal to one-half or more of its length.

As the calyx breaks, the color is between off-white and Brilliant Yellow Green, 2.5GY9/8. The inner surface of the sepals carries a wooly tomentum; margins are lined with stipitate glands.

As the first petal opens, the bud is average in size, medium-length, pointed and ovoid. The color on the outside and inside of the petal is the same, with a basal attachment point of near Brilliant Yellow Green, 2.5GY9/8, suffusing to between off-white and Brilliant Yellow Green, 2.5GY9/8. The bud opens up well, and is not prevented from opening by cold, hot, wet or dry weather.

BLOOM

When fully open, the bloom is of average size, being from 3 to 3½ inches in diameter. The petalage is double, with from 25 to 30 petals, plus from 0 to 5 petaloids arranged regularly. In form, the bloom is cupped to high centered at first, becoming cupped, the petals remaining at first tightly cupped, becoming later at maturity loosely cupped, with tips reflexed outward.

The petals are of medium thickness, with inside satiny and outside slightly shiny. The outside petals are from round to broadly obovate, the apex usually having one notch. Intermediate petals are broadly obovate, with apex rounded. The inside petals are obovate to irregular. Color may be modified by being shaded and/or washed with other colors.

The following description is of a newly opened rose that had been grown outdoors in the month of September, in Ontario, Calif.

The outer surface and inner surface of the outside petal were of the same coloration, there being a basal attachment point which was near Brilliant Greenish Yellow, 10Y9/9, suffusing to between off-white and Brilliant Greenish Yellow, 10Y9/9. The intermediate and inside petals were of the same coloration as the outside petals.

The following description was made from a rose that was open for three days outdoors in the month of September. The plant had been grown in Ontario, Calif.

Both the outside petal and the inside petal were of the same coloration. The outer surface had a basal attachment point which was near Brilliant Greenish Yellow, 7.5Y9/8, suffusing quickly to between white and off-white, with only the slightest shade of near Brilliant Greenish Yellow, 7.5Y9/8. The inner surface was the same coloration but with more pure white pigment.

The general color effect of the newly opened flower was near off-white, with some suffusing to between Brilliant Greenish Yellow, 7.5Y9/8, and Brilliant Yellow, 2.5Y9/9, in the depths of the flower. After being three days open, the flower was more near white, with some suffusing to between off-white and Brilliant Yellow, 2.5Y9/9, in the depths of the flower. Some petals drop off cleanly; some persist, fading to between white and off-white. They are not particularly affected by cold, hot, wet or dry weather.

The flower on the bush in the garden persists for from 3 to 4 days in the month of September. Cut roses grown outdoors and kept at living-room temperatures last from 3 to 4 days in the month of September.

REPRODUCTIVE ORGANS

There are an average number of stamens arranged regularly about the pistils.

Filaments are medium-length to long and near Brilliant Greenish Yellow, 10Y9/9, in color. Most are with anthers.

Anthers are of medium size and all open approximately at once. Their color is lighter than Brilliant Yellow, 5Y9/9, just prior to dehiscence.

Pollen is somewhat sparse, and much lighter in color than Brilliant Yellow, 5Y9/9.

There are from an average number to many pistils, there being approximately 110.

Styles are very uneven, of average length, very thin and loosely bunched. Their coloration is near Brilliant Yellow Green, 2.5GY9/8.

The stigma is near Strong Red, 2.5R5/12, in color.

The ovaries are usually all enclosed in the calyx.

Since this variety does not normally produce hips when grown outdoors in Ontario, Calif., there are no hips or seeds for description.

FOLIAGE

The compound leaves usually comprise from three to five leaflets. They are from normal to abundant, of medium size, moderately heavy and semi-glossy. The leaflets are round to ovate in shape, with apex mucronate, base round and margin doubly serrate.

The upper surface of the mature foliage is a color between Moderate Olive Green, 5GY4/3, and Dark Grayish Green, 10GY3/2. The under surface is between gray and Moderate Olive Green, 5GY4/3, in coloration.

The young foliage had the same coloration on both the upper and under surface, this being near Strong Yellow Green, 7.5GY6/8, washed and edged with near Moderate Reddish Brown, 7.5R3/6.

The rachis is average in size, grooved on its upper side, with some stipitate glands on the edges. The under side is moderately smooth and has a few stipitate glands.

The stipules are medium-length and medium-width, with medium-length to long points recurved toward the stem.

The plant displays a more than average resistance to mildew as compared with similar varieties now in commerce grown under comparable conditions.

GROWTH

The plant is bushy and upright-spreading in habit, and much branched. It displays a moderately vigorous growth. Canes are of light to medium caliper.

The main stems are between Moderate Yellow Green, 2.5GY5/5, and Light Olive, 10Y5/5, in color. They bear few large prickles, which are short to medium-length, almost straight to hooked slightly downward, and with a medium-length narrow base. Their color is between Strong Brown, 5YR4/5, and Moderate Brown, 5YR3/3. There are no small prickles and no hairs.

The branches have a coloration which is between Moderate Yellow Green, 5GY5/6, and Moderate Olive Green, 7.5GY4/4. They carry very few large prickles, which are moderately short, almost straight to hooked slightly downward, with a short narrow base. Their coloration is near Strong Brown, 5YR4/5. There are no small prickles and no hairs.

The new shoots are between Strong Yellow Green, 5GY7/10, and Strong Yellow Green, 7.5GY6/8, in color. They bear very few large prickles, which are moderately short, almost straight to hooked slightly downward, with a short narrow base. Their color is near Strong Yellow Green, 2.5GY6/8. There are no small prickles and no hairs.

We claim:

1. A new and distinct variety of rose plant of the hybrid grandiflora class, substantially as herein shown and described, being further especially characterized in the vigor of its growth habit, being much branched, and clothed in semi-glossy relatively disease-resistant foliage, the flowers being off-white in coloration, well-formed, and of a strong citrus fragrance.

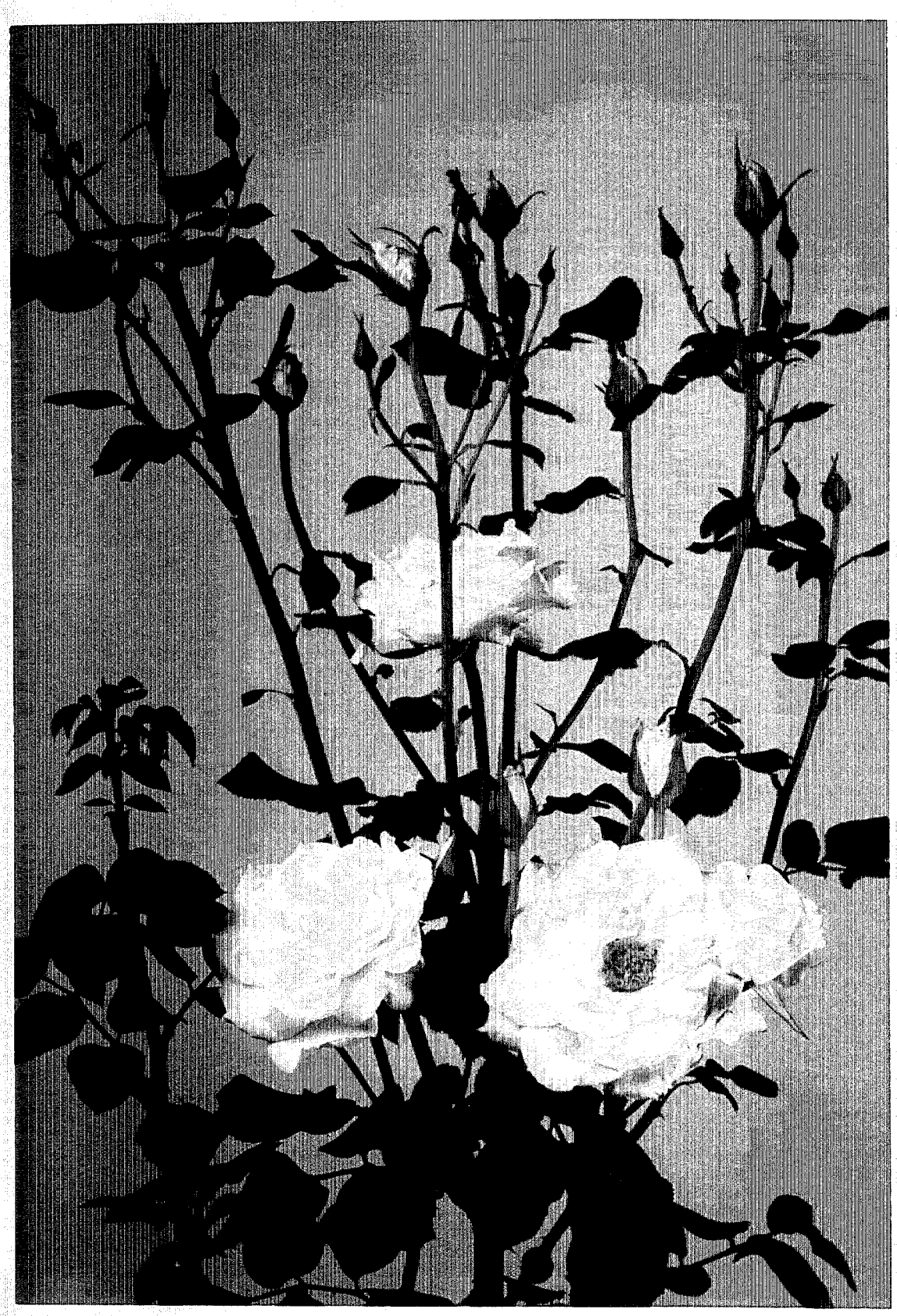

* * * * *